US012622574B2

(12) United States Patent
Van Ness et al.

(10) Patent No.: US 12,622,574 B2
(45) Date of Patent: May 12, 2026

(54) ARTICULATING MEDICAL INSTRUMENT

(71) Applicant: GYRUS ACMI, INC., Westborough, MA (US)

(72) Inventors: David Van Ness, Salt Lake City, UT (US); Maria G. Benson, West Boylston, MA (US); Mayur K. Patel, Framingham, MA (US); Ronald Ciulla, Westford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 161 days.

(21) Appl. No.: 17/659,915

(22) Filed: Apr. 20, 2022

(65) Prior Publication Data

US 2022/0338718 A1 Oct. 27, 2022

Related U.S. Application Data

(60) Provisional application No. 63/180,278, filed on Apr. 27, 2021.

(51) Int. Cl.
*A61B 1/005* (2006.01)
*A61B 1/008* (2006.01)
*A61M 25/01* (2006.01)

(52) U.S. Cl.
CPC .......... *A61B 1/0055* (2013.01); *A61B 1/0057* (2013.01); *A61M 25/0138* (2013.01)

(58) Field of Classification Search
CPC ................ A61B 1/0055; A61B 1/0057; A61B 2017/00309; A61M 25/0138; A61M 25/0013; A61M 25/0053; A61M 25/0054
See application file for complete search history.

(56) References Cited

U.S. PATENT DOCUMENTS 3,998,216 A 12/1976 Hosono
5,437,288 A 8/1995 Schwartz et al.
(Continued)

FOREIGN PATENT DOCUMENTS

CN 105828866 A 8/2016
CN 115245304 10/2022
(Continued)

OTHER PUBLICATIONS

"Japanese Application Serial No. 17 690,500, Office Action mailed May 16, 2023", w English Translation, 4 pgs.
(Continued)

*Primary Examiner* — Anh Tuan T Nguyen
*Assistant Examiner* — Rynae E Boler
(74) *Attorney, Agent, or Firm* — Schwegman Lundberg & Woessner, P.A.

(57) ABSTRACT

A patterned tube for use with a scope or similar medical device can include at least one flexible section. The at least one flexible section can include a plurality of first cuts having a first thickness, a plurality of second cuts having a second thickness. Particular ones of the plurality of second cuts can be located substantially opposite particular ones of the plurality of first cuts. The at least one flexible section can further include a plurality of bending moment transfer portions. Particular ones of the bending moment transfer portions can be located between particular ones of the first cuts and particular ones of the second cuts.

23 Claims, 14 Drawing Sheets

(56) References Cited

U.S. PATENT DOCUMENTS

| | | | |
|---|---|---|---|
| 5,477,856 | A | 12/1995 | Lundquist |
| 6,270,453 | B1 | 8/2001 | Sakai |
| 6,511,471 | B2 | 1/2003 | Rosenman et al. |
| 6,551,271 | B2 | 4/2003 | Nguyen |
| 6,749,560 | B1 | 6/2004 | Konstorum et al. |
| 6,835,173 | B2 | 12/2004 | Couvillon, Jr. |
| 6,837,867 | B2 | 1/2005 | Kortelling |
| 7,637,903 | B2 | 12/2009 | Lentz et al. |
| 7,637,905 | B2 | 12/2009 | Saadat et al. |
| 8,037,590 | B2 | 10/2011 | Macnamara |
| 8,052,597 | B2 | 11/2011 | Boulais |
| 8,118,732 | B2 | 2/2012 | Banik et al. |
| 8,409,114 | B2 | 4/2013 | Parins |
| 8,535,219 | B2 | 9/2013 | Banik et al. |
| 8,684,967 | B2 | 4/2014 | Engel et al. |
| 8,911,814 | B2 | 12/2014 | Chen |
| 9,198,561 | B2 | 12/2015 | Smith et al. |
| 9,215,970 | B2 | 12/2015 | Boutillette et al. |
| 9,545,249 | B2 | 1/2017 | Cole et al. |
| 9,750,567 | B2 | 9/2017 | Falwell et al. |
| 9,795,765 | B2 | 10/2017 | Romoscanu |
| 9,808,595 | B2 | 11/2017 | Turnlund et al. |
| 9,820,635 | B2 | 11/2017 | Seto et al. |
| 10,039,918 | B2 | 8/2018 | Foster et al. |
| 10,321,804 | B2 | 6/2019 | Jacobsen et al. |
| 10,675,444 | B2 | 6/2020 | Kauphusman et al. |
| 2004/0181174 | A2* | 9/2004 | Davis .................... A61M 25/09 |
| | | | 600/585 |
| 2004/0199052 | A1 | 10/2004 | Banik et al. |
| 2004/0249367 | A1 | 12/2004 | Saadat et al. |
| 2005/0131279 | A1 | 6/2005 | Boulais et al. |
| 2005/0197536 | A1 | 9/2005 | Banik et al. |
| 2006/0189896 | A1* | 8/2006 | Davis ................ A61M 25/0054 |
| | | | 600/585 |
| 2007/0208224 | A1 | 9/2007 | Olson |
| 2007/0260225 | A1* | 11/2007 | Sakakine .......... A61M 25/0147 |
| | | | 604/528 |
| 2008/0300462 | A1 | 12/2008 | Intoccia et al. |
| 2009/0043372 | A1* | 2/2009 | Northrop ........ A61M 25/09016 |
| | | | 623/1.15 |
| 2009/0192495 | A1 | 7/2009 | Ostrovsky et al. |
| 2010/0286626 | A1 | 11/2010 | Petersen et al. |
| 2011/0082337 | A1 | 4/2011 | Boulais |
| 2013/0197306 | A1 | 8/2013 | Armand et al. |
| 2014/0023428 | A1 | 1/2014 | Kappel et al. |
| 2014/0066952 | A1 | 3/2014 | Kappel et al. |
| 2014/0234280 | A1 | 8/2014 | Schlievert et al. |
| 2014/0234281 | A1 | 8/2014 | Berenson et al. |
| 2014/0234282 | A1 | 8/2014 | Cohen et al. |
| 2014/0234283 | A1 | 8/2014 | Schonberger |
| 2014/0234284 | A1 | 8/2014 | Schonberger et al. |
| 2014/0234285 | A1 | 8/2014 | Im et al. |
| 2014/0234286 | A1 | 8/2014 | Kitagawa et al. |
| 2014/0234287 | A1 | 8/2014 | Hajjar et al. |
| 2014/0234288 | A1 | 8/2014 | Grabowski |
| 2014/0234289 | A1 | 8/2014 | Liu et al. |
| 2014/0249550 | A1 | 9/2014 | Mullins et al. |
| 2014/0336685 | A1 | 11/2014 | Podmore et al. |
| 2016/0135665 | A1 | 5/2016 | Fleury et al. |
| 2016/0310701 | A1 | 10/2016 | Pai |
| 2017/0340862 | A1 | 11/2017 | Calabrese et al. |
| 2019/0231169 | A1* | 8/2019 | Thissen ............. A61M 25/0013 |
| 2022/0105312 | A1* | 4/2022 | Davis ................ A61M 25/0053 |

FOREIGN PATENT DOCUMENTS

| | | |
|---|---|---|
| DE | 102022109839 | 10/2022 |
| JP | S58159719 | 9/1983 |
| JP | 2010535587 | 11/2010 |
| JP | 2019527099 | 9/2019 |
| JP | 2022169481 | 11/2022 |
| JP | 7401591 B2 | 12/2023 |
| JP | 2024019439 A | 2/2024 |
| JP | 7671332 B2 | 4/2025 |
| JP | 2025100782 A | 7/2025 |
| WO | WO-2013164682 A1 | 11/2013 |
| WO | 2016052145 | 4/2016 |

OTHER PUBLICATIONS

"Japanese Application Serial No. 17 690,500, Response filed Jul. 4, 2023 to Office Action mailed May 16, 2023", w english claims, 10 pgs.

"Chinese Application Serial No. 202210451219.8, Notification to Make Rectification mailed Jun. 10, 2022", with machine translation, 3 pgs.

"Chinese Application Serial No. 202210451219.8, Response filed Jul. 1, 2022 to Notification to Make Rectification mailed Jun. 10, 2022", with machine translation, 4 pgs.

"German Application Serial No. 102022109839.7, Office Action mailed Jul. 4, 2022", with machine translation, 4 pgs.

"German Application Serial No. 102022109839.7, Response filed Jul. 19, 2022 to Office Action mailed Jul. 4, 2022", with machine translation, 74 pgs.

"Chinese Application Serial No. 202210451219.8, Office Action mailed Mar. 26, 2025", w/ English translation, 20 pgs.

"Chinese Application Serial No. 202210451219.8, Response filed Sep. 29, 2025 to Office Action mailed Mar. 26, 2025", w/ English Claims, 16 pgs.

* cited by examiner

ARTICULATING MEDICAL INSTRUMENT

CROSS-REFERENCE TO RELATED APPLICATION

This application claims the benefit of priority to U.S. Provisional Patent Application Ser. No. 63/180,278, filed Apr. 27, 2021, the contents of which are incorporated herein by reference in their entirety.

TECHNICAL FIELD

The present disclosure relates to an articulation section of a medical scope.

BACKGROUND

Flexible scopes such as flexible endoscopes are used for diagnostic and therapeutic medical procedures, for example, procedures inside a human or animal digestive system, or inside the abdomen. Portions of the scope, such as the distal end of the scope, can be made flexible such as to allow a surgeon to bend or otherwise articulate the scope to access a particular target anatomy.

SUMMARY

Endoscopes and other similar surgical scopes or catheters can be used in a variety of surgical procedures, for example, in ear, nose, and throat (ENT) procedures such as a tonsillectomy, sinus surgery, or other similar procedures, procedures in the digestive system, or procedures inside the abdomen. Catheters can be used in procedures such as inserting stents or balloons into arteries. Often, during a surgical procedure, it may be desired that at least a portion of the scope can be articulated so as to be angled (e.g., bent) from a straight, zero degrees, to an angle such as fifteen degrees, thirty degrees, forty five degrees, ninety degrees, two hundred degrees, or greater. The sheath or tube (e.g., such as a hypotube or hypodermic tube or other cylindric or non-cylindric tube, such as having a particular inner and outer diameter or similar lateral dimension) of the scope or catheter can be made of or formed from a rigid material such as surgical grade stainless steel, an alloy, or another similar material capable of being made flexible and flexing or bending at an angle. Such flexibility can be attained by forming a series of cuts (e.g., laser cuts) in the tube. Different types of cuts in the tube can be utilized (e.g., finer or thinner cuts, coarser or wider cuts, or the like), with each type of cut having its particular characteristics. For example, different types of cuts (e.g., different cut widths) can impact the degree to which the flexible portion of the tube can be bent, the amount of torque that the tube can sustain, compressive effects under load, or the like.

One way to address these issues is to use a combination of course cuts and fine cuts in a portion of the tube or sheath of the scope, a patterned tube deflectable section of a medical device that can be connected to a scope to be made flexible. In an example, coarse and fine cuts can be alternated, such as to help achieve a large angular degree of articulation and reduce or minimize compressive effects under load of the cuts by staying within the elastic material property region of the material. The depth, width, length, and number of cuts can be varied to achieve the desired degree of articulation, articulated shape, initiation of articulation, articulation sweep (e.g., the path the distal tip of the scope travels from a starting position to an ending or maximally articulated position), etc., of the most distal end of the flexible or bendable portion. The backbone of the tube can be segmented into a number of regions, segments, or sections with each region containing a number of cuts to make the region flexible. The cuts can be achieved, for example, by laser cutting a "pattern" in the regions of the tube. The cut tube can then be electropolished or otherwise smoothed, such as to help remove any sharp edges and/or burrs on the edges of the cuts.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
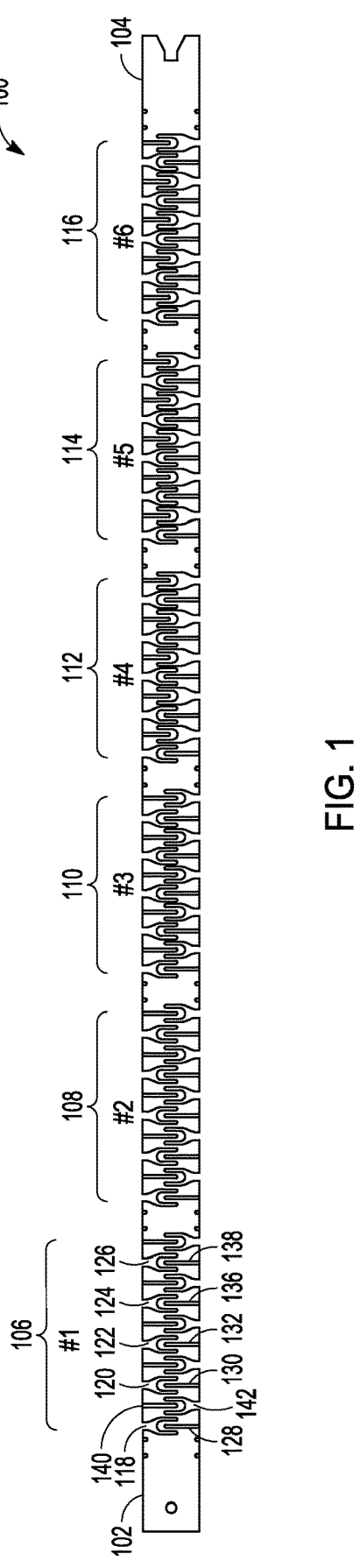
FIG. 1 illustrates an example of a backbone of a tube with multiple regions containing alternating fine and coarse cuts.

This document describes, among other things, an articulating medical instrument. For example, disclosed herein are systems for a hybrid alternating fine cut and coarse cut articulating section of a tube for attachment to a medical scope such as an endoscope. The system can include a tube formed from a solid material (e.g., surgical stainless steel or the like), the tube having an inner diameter and an outer diameter. At least one deflectable or other flexible segment or other section can be formed in the tube. Each segment can include a plurality of first slits, cuts, or other openings having a first thickness or width (e.g., coarse cuts), and a plurality of second slits, cuts, or other openings having a second thickness or width (e.g., fine cuts). In an example, a particular one of the coarse cuts can be located opposite (e.g., across the tube from) a particular one of the fine cuts and adjacent to a different particular one of the fine cuts. The coarse cuts can have a greater width than the opposing fine cuts. For example, the coarse cuts can have a width of 0.015 or 0.016 inches and the fine cuts can have a width of 0.003 inches. The width of any of the coarse or fine cuts can be specified at any thickness and separation distance between adjacent cuts desired for the tube, or a portion of the tube, to achieve a particular "bend" angle of articulation.

Similarly, the tube can have as many flexible segments as desired for the particular use, procedure, application, or the like, for which the tube will be implemented. Likewise, each segment can have as many coarse cuts and fine cuts as desired such as to achieve a direction of articulation (e.g., two-way articulation, four-way articulation, etc.), or a particular angle of articulation (e.g., 90-degrees, 260-degrees, 300-degrees, etc.). The coarse cuts and corresponding fine cuts can be formed in the tube such that a switchback member (e.g., "u shaped" portion or bend conforming to or defining a circumference, periphery, or similar surface of a backbone of the tube) is formed, such as between respective coarse cuts and their corresponding fine cuts. The switchback members can force the opposing cuts to open or close during articulation of the backbone of the tube.

In an example, the cuts may be pulled closed using an articulation member such as a cable or wire or "pull wire". In an example, one or more pull wires can be attached or guided (e.g., slidably) to the inside of a portion of the tube (e.g., a wider portion, an outer edge of the inner diameter, or any other internal portion of the tube as desired or suitable). Pull wire mounts can be located on an internal portion of the tube. Such pull wire mounts can allow an associated pull wire to pass therethrough from the proximal end to the distal end of the tube. This can suitably maintain the position of the pull wire along the flexible section, such as to enable deflection or bending of the distal end when the pull wire is retracted via a handle or other pull wire manipulator. There can be as many pull wires as desired for the particular device, depending, in part, on how many directions the device is to deflect or bend. For example, there can be two pull wires on opposing sides for a two-way deflectable device, four pull wires for a four-way deflectable device, or the like.

In an example, during articulation of the backbone, coarse cuts can be pulled closed as the backbone is bent. For example, during articulation, a coarse cut may be "pulled closed" to a width or thickness of 0.0077 inches from its neutral thickness or width (e.g., 0.015 inches). Bending moments can be transferred through transfer members (e.g., central "beams") located in the backbone. For example, bending moments can be transferred between adjacent coarse cuts, between adjacent fine cuts, or both, to the switchback members. This can force the fine cuts to open as the coarse cuts are pulled closed. Conversely, as the fine cuts are pulled closed, the switchback members can force the opposing coarse cuts to open (e.g., to a width or thickness of 0.019 inches from a neutral thickness or width of 0.015 inches). The fine cuts can be pulled open wider (e.g., to a width of 0.0072 inches from a neutral width of 0.003 inches) or forced narrower (e.g., to a width of 0.0020 inches from a neutral width of 0.003 inches) depending on how the backbone of the tube is being articulated. The starting or neutral width of the coarse or the fine cuts can vary at different locations on the tube. Similarly, the width to which the cuts can be biased open or closed during articulation of the backbone can vary. The stiffness of the central beams or other transfer members can also be varied in particular adjacent sections of the backbone, such as to allow for selection of adjustment of the sweep path, the intermediate and final positions of the endoscopic tip, or the like.

Forming the switchback members between the coarse cuts and the fine cuts can help provide increased articulation capability of the flexible portion of the tube and allows the backbone to have a smaller radius of curvature for a given backbone length (versus uncut stainless steel backbone designs) without causing plastic deformation. This smaller radius of curvature can be desirable for an endoscope in some applications or procedures such as to help improve access to certain parts of anatomy with the distal portion of the scope (e.g., the lower calyx in a kidney).

A patterned tube for permitting articulation (bending) can include at least one flexible section along at least a portion of a length of the tube, the length of the tube spanning from a proximal end of the tube to a distal end of the tube. The flexible section can include multiple first cuts having a first cut thickness and multiple second cuts having a second cut thickness. Particular ones of the second cuts can be located substantially opposite laterally across the tube from particular ones of the first cuts. The particular second cuts can be in alignment with the particular first cuts, or alternatively, can be offset from the particular first cuts. The particular first cuts and second cuts can be separated by switchback members.

The tube may further comprise one or more bending moment transfer members located between adjacent particular ones of the first cuts and adjacent particular ones of the second cuts and connect adjacent switchback members. One or more bending moment transfer members can respectively include a circumferential portion extending about an outer circumference of the tube configured to transfer a bending moment to a switchback member formed in the tube between a particular one of the first cuts and a particular one of the second cuts. The switchback member can be configured to cause a particular first cut to do one of widen or narrow and cause an opposing particular second cut to do the other of widen or narrow during an articulation of a portion of the tube including the particular first cut and the opposing particular second cut. Stated differently, as the tube is bent or articulated, a switchback member that is located between a first cut and a second cut can cause one of these cuts to open and the opposing cut to close, or vice-versa.

The tube can further include an articulation member such as a cable or a wire. The articulation member can be attached to an interior portion within an inner lumen of the tube by at least one guide configured to maintain a position of the articulation member along the flexible section. Constrained by the at least one guide, the articulation member can help enable deflection of at least a portion of the flexible section when the articulation member is pulled or retracted, such as via a handle, a pull wire, or other manipulator.

The tube can comprise multiple flexible sections, such as a first flexible section and a second flexible section, such as with the second flexible section located adjacent to the first flexible section. In an example, at least a portion of the second flexible section can be constructed with features (e.g., switchback members, cuts, or the like) arranged at a rotational angle with respect to similar features in the first flexible section. In an example, the first flexible section can be formed from a different material than the second flexible section, such that the material of the first flexible section and the second flexible section have a different flexibility.

In an example a thickness of the wall of the tube can be varied to help provide differing amounts of flexibility in different areas of the flexible sections of the tube. For example, an outer diameter toward or at the distal end of the flexible section can be smaller than the outer diameter toward or at the proximal end of the flexible section. In this example, the wall thickness of the cylinder can be thinner at the distal end of the flexible section relative to a more proximal portion. Such a change in the thickness of the wall of the tube can be abrupt (e.g., a "step" changing from a thickness of "x" centimeters or inches to 0.75x centimeters or inches at a certain point), or may include a gradual tapered change in which the thickness of the wall of the tube begins to decrease, linearly or non-linearly, toward the distal end or toward some point near the distal end of the flexible section.

The thinner wall at or toward the distal end can provide additional flexibility of the tube in addition to what the cut pattern can provide. This change in thickness can be accomplished on a single-piece tube or a similar change in flexibility can be achieved by forming a tube with two or more segments of a different flexibility and/or a different material composition welded or otherwise connected together (e.g., in adjacent sections).

FIG. 1 illustrates an example of a backbone of a tube with multiple regions, a particular region containing alternating fine and coarse cuts. FIG. 1 illustrates an example of a patterned tube 100 having a proximal end 102 and a distal end 104. The patterned tube 100 includes a first flexible segment 106, a second flexible segment 108, a third flexible segment 110, a fourth flexible segment 112, a fifth flexible segment 114, and a sixth flexible segment 116. The flexible segments 106-116 can extend along at least a portion of the length of the patterned tube 100 from the proximal end 102 to the distal end 104. The flexible segments 106-116 can be located substantially adjacent to one another along the length of the patterned tube 100. For example, the first flexible segment 106 can be adjacent to the second flexible segment 108 which can be adjacent to the third flexible segment 110, and so on.

The flexible sections 106-116 can include multiple (first) coarse cuts 118, 120, 122, 124, and 126 having a first cut thickness, and multiple (second) fine cuts 128, 130, 132, 134, and 138 having a second cut thickness. A particular fine cut of the multiple fine cuts 128-138 can be located in alignment substantially opposite laterally across the patterned tube 100 from a particular coarse cut of the multiple coarse cuts 118-126. For example, coarse cut 118 and fine cut 128 can be located substantially opposite laterally across from each other. Similarly, coarse cut 120 can be located substantially opposite laterally across from fine cut 130, and so on. Alternatively, a particular fine cut of the multiple fine cuts 128-138 can be located across the patterned tube 100, but offset from, a particular coarse cut of the multiple coarse cuts 118-126. In an example, the pattern of coarse cuts and fine cuts can be formed on opposing sides of the cylinder forming the patterned tube 100, such that on one side of the cylinder, there will be a particular fine cut between two particular coarse cuts. The cut cylinder of the patterned tube can be referred to as its cylindrical backbone. For example, as illustrated in FIG. 1, on one side of the tube, cut 118, which is a particular coarse cut of the multiple coarse cuts with the first cut thickness is adjacent to cut 140 which has a second cut thickness. The cut 140 having the second cut thickness is adjacent to cut 120 which again has the first cut thickness. Similarly, on the opposing side of the cylinder, cut 142 having the first cut thickness is between cuts 128 and 130, which each have the second cut thickness. A similar pattern of cuts may be formed in each of the flexible segments.

Figure 2A:
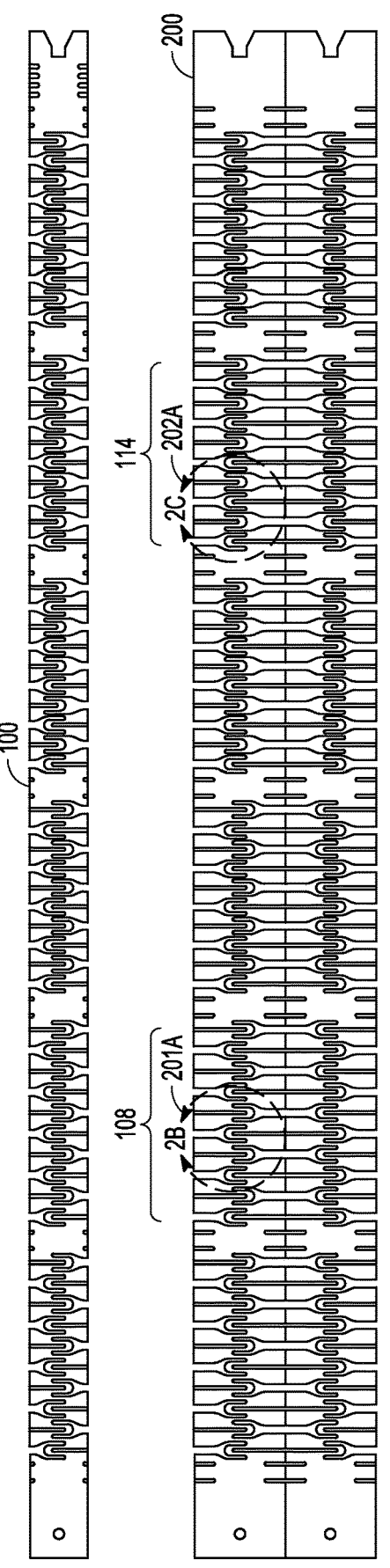
FIGS. 2A-2D illustrate alternate views of the tube of FIG. 1 including a view of the tube laid flat and zoomed in detailed views of the cuts and switchback members formed between the cuts.
Figure 2C:
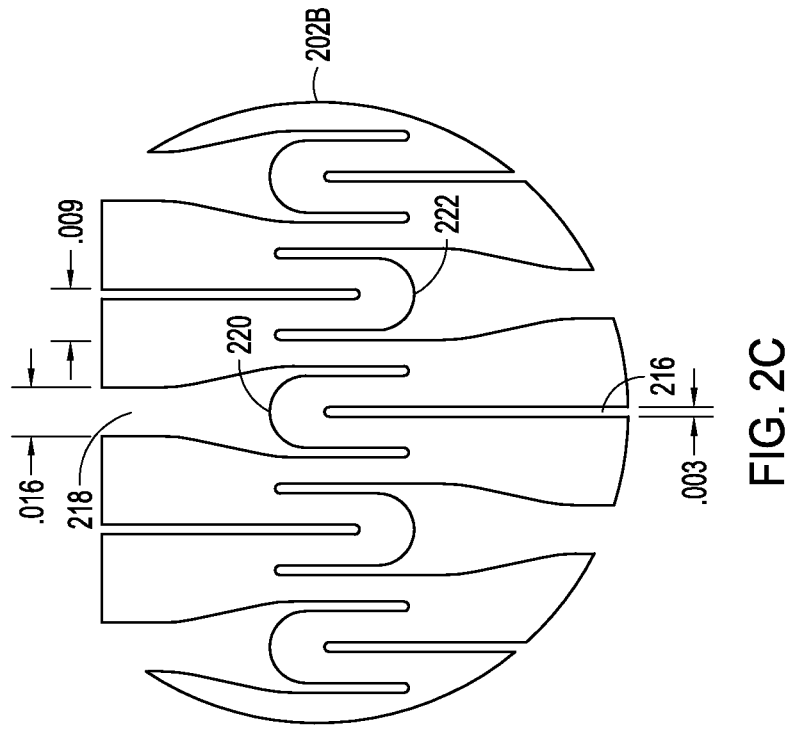
Figure 2B:
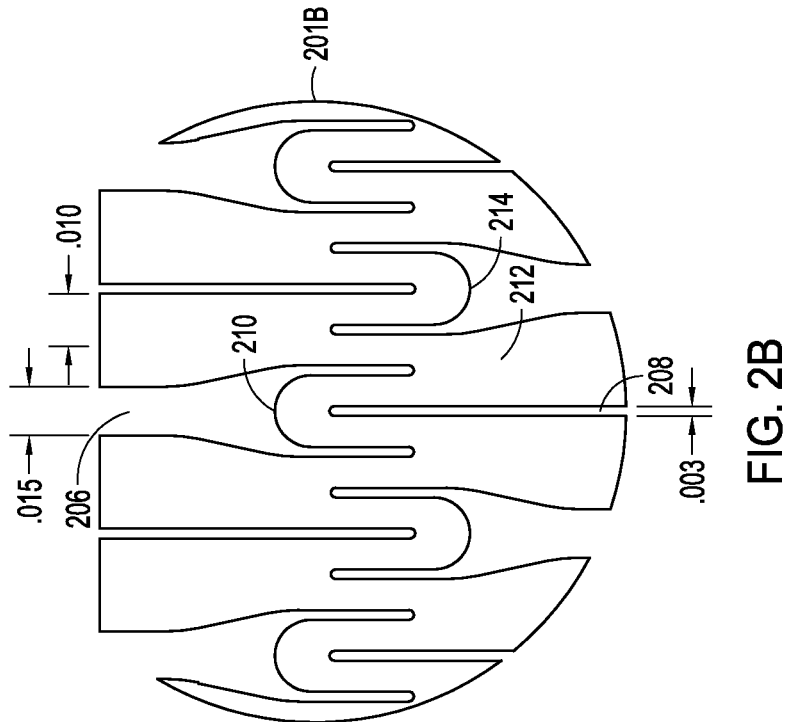

FIGS. 2A-2D illustrates alternate views of the tube of FIG. 1 including a conceptual view of the tube in which the cylinder is conceptually cut lengthwise and "unrolled" and laid flat and zoomed in to provide more detailed views of the cuts and switchback members formed between the cuts. FIG. 2A again shows the patterned tube 100 of FIG. 1, and illustrates an example of the patterned tube 100 conceptually "unrolled" and flattened such that it is no longer in a three-dimensional cylindrical shape. The unrolled tube 200 includes the second flexible segment 108, Detail A 201A marked by the circle in the second flexible segment 108, the fifth flexible segment 114, and Detail B 202A, marked by the circle in the fifth flexible segment 114. Detail A 201A and Detail B 202A are magnified to a 16:1 scale in FIGS. 2B and 2C respectively. As illustrated in FIG. 2B, the enhanced view of Detail A 201A an example width of coarse cut 206 can be 0.15 inches, and an example width of the corresponding fine cut 208 can be 0.003 inches. Switchback members can be formed between opposing first cuts and second cuts. For example, first switchback member 210 can be formed between coarse cut 206 and fine cut 208. Similarly, a second switchback member 214 can be formed adjacent to the first switchback member 210.

Unrolled, the switchback members can be formed in a u-shape (e.g., a horseshoe shape), however the switchback members can be another or different shape. For example, unrolled, a particular switchback member can be triangular shaped (e.g., "V" shaped), rectangular, an octagon, or any suitable shape such as to achieve a desired bending force or degree of deflection of the respective cuts between which the switchback member is formed. In an example, the shape of the switchback members on one portion of the patterned tube 100 can be different than on another portion of the patterned tube 100. For example, in the first flexible segment 106 the switchback members can be u-shaped (unrolled) while the switchback members in the second flexible segment 108 can be triangular (unrolled), and the switchback members in the third flexible segment 110 can be rectangular (unrolled). Similarly, the size (e.g., a width, a different radius of the switchback shape, etc.) of the switchback members along the patterned tube 100 can be selected or varied such as to help meet a desired degree of deflection of the fine and coarse cuts.

The cut pattern described above can provide adjacent switchback members being offset and oriented opposite to each other. For example, the unrolled u-shaped "bend" of the first switchback member 210 can be oriented in the opposite direction (e.g., face, point, etc.) than that of the second switchback member 214, such that when the patterned tube 100 is "unrolled" and laid flat as illustrated in FIG. 2A and shown in Detail A 201A as enhanced in FIG. 2B, the first switchback member 210 can appear concave upward and the second switchback member 214 can appear concave downward. In another example, a distance or length of the cut into the switchback segments can be determined or specified to control the flexibility at that point. For example, the "end" of fine cut 216 in FIG. 2C can be "y" units to the "end" of the concave down portion of switchback member 220. Thus, to adjust the flexibility of switchback member 220, the distance "y" can be modified so that the end of the cut 216 is closer to the "tip" of the concave downward portion of the switchback member 220 (resulting in the "length" of cut 216 being greater). The further the cut 216 is made into the switchback member 220, the greater the amount of flexibility the patterned tube 100 has at the switchback member 220.

As illustrated in FIG. 2B, bending moment transfer member 212 can be located between adjacent coarse cuts and adjacent fine cuts to connect adjacent switchback members, such as first switchback member 210 and the second switchback member 214. The bending moment transfer member 212 can include a circumferential portion, such as extending about an outer circumference of the patterned tube 100, and can be configured to transfer a bending moment to the switchback members, such as to the first switchback member 210 and/or second switchback member 214.

In an example, the thickness or width of particular coarse cuts can vary along the length of the patterned tube 100. For example, as illustrated in FIG. 2C, in the absence of bending, coarse cut 206 located in the second flexible segment 108 of the patterned tube 100 can have a neutral thickness or width of 0.015 inches, and as illustrated in FIG. 2C, coarse cut 218 located in the fifth flexible segment 114 can have a neutral thickness or width of 0.016 inches. This can result in the size of the bending moment transfer members between adjacent switchback members as well as the width of the switchback members being varied at different portions along the patterned tube 100. For example, in FIG. 2B, the width of one "side" of switchback member 214 is 0.010 inches, while in FIG. 2C, the width of one "side" of switchback member 222 is 0.009 inches.

Figure 2D:
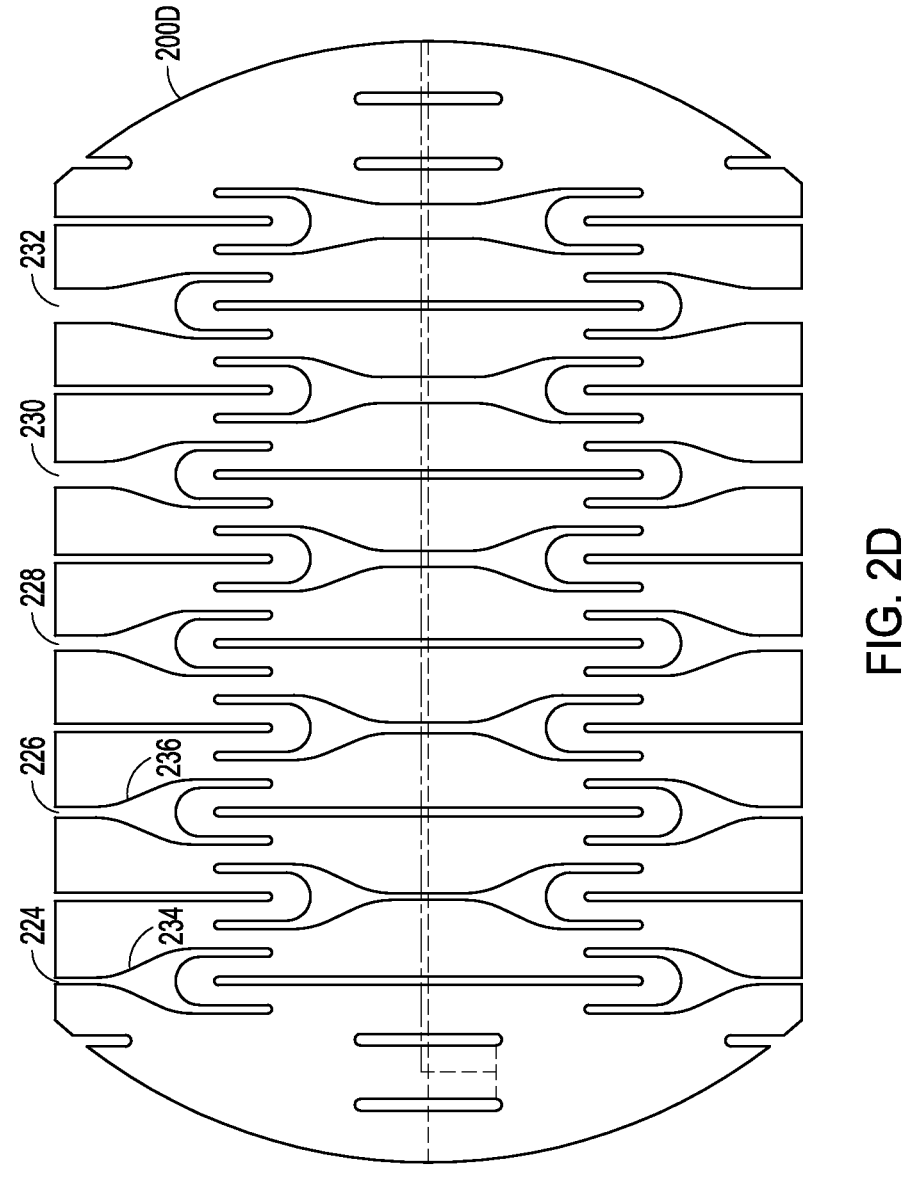

In an example, as illustrated in FIG. 2D, which illustrates a magnified portion 200D of the unrolled tube 200, the coarse cuts can vary in width along the length of the tube. For example, the coarse cuts can be wider or thicker when encountered in a direction from the proximal end to the distal end. As illustrated in the magnified portion 200D, coarse cut 232 is wider than coarse cut 230, which is wider than coarse cut 228, etc. It is also understood that the opposing fine cuts can be made wider in a similar sequence or manner to the coarse cuts, or the fine cuts may maintain the same width along the length of the flexible segment and/or the length of the tube. Thus, in such an example, the more distal the portion of the flexible section, the larger the width of the "gap" or opening of the coarse cuts are and hence the more articulation can be achieved. Stated differently, the distal portion of the flexible section can deflect more than or to a greater angle than the proximal end of the flexible section. This can allow the distal portion to bend more sharply allowing a scope to contact harder-to-reach portions of anatomy such as the lower calyx of the kidney.

In such an example in which the width of the cuts are varied or changed from the proximal end to the distal end of a flexible section, the change can be gradual (e.g., a linear change in gap size from the first cut on the proximal end to an "nth" cut on the distal end, or a non-linear (e.g., exponential)) change, or a more gradual change. In another example, the change can be sudden, such as abruptly switching from a uniform first gap size to a larger, second gap size. The gap size of the coarse cuts and/or the fine cuts can be varied in any pattern such as with the gap size of one or more of the cuts in the distal portion being wider than the gap size of one or more of the cuts in the proximal portion.

In an example, at least one portion of a particular coarse cut or a particular fine cut can be tapered to accommodate a particular switchback member. For example, as shown on the magnified portion 200D, coarse cuts 224, 226, 228, 230, and 232, can include a tapered portion such as tapered portion 234 on cut 224, or tapered portion 236 on cut 226. An amount of taper can depend on the width of the cut on which the taper is included.

Figure 3A:
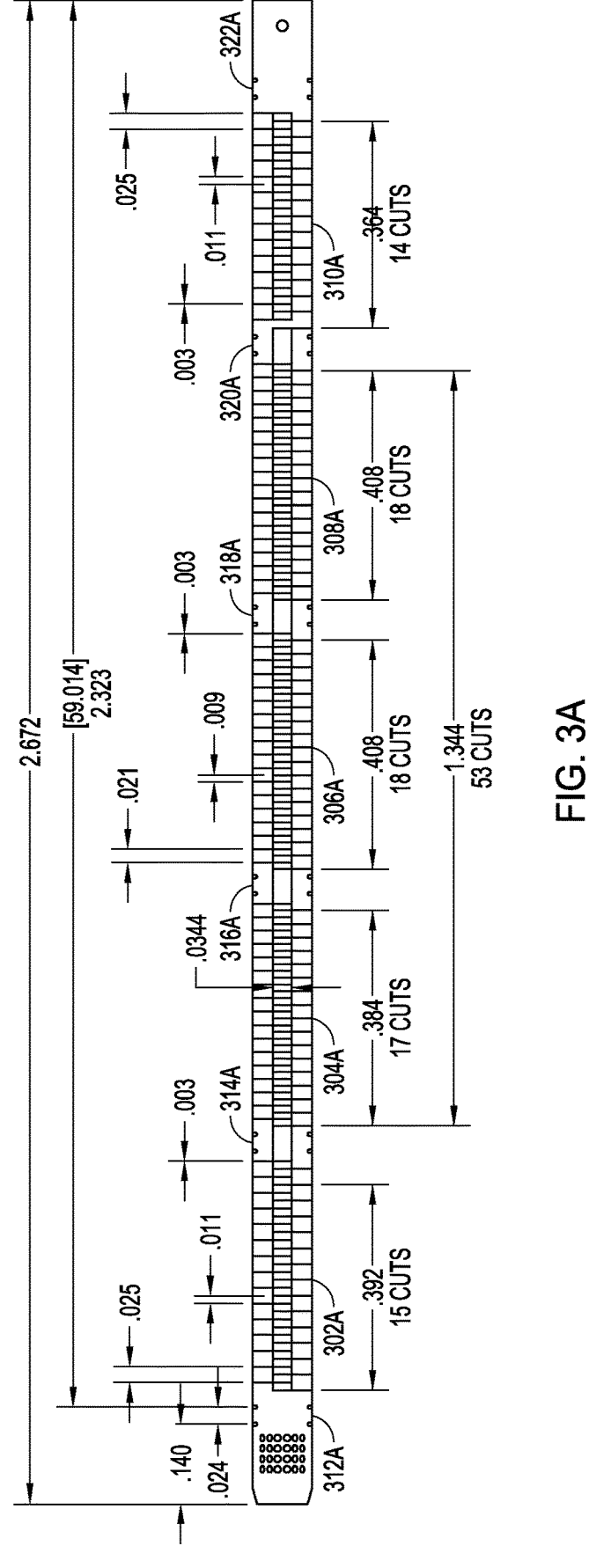
FIGS. 3A-5B illustrate examples of tubes with a varying number of flexible sections containing different numbers of cuts, different cut widths, and a different number of wire guides to achieve different angles of articulation.
Figure 3B:
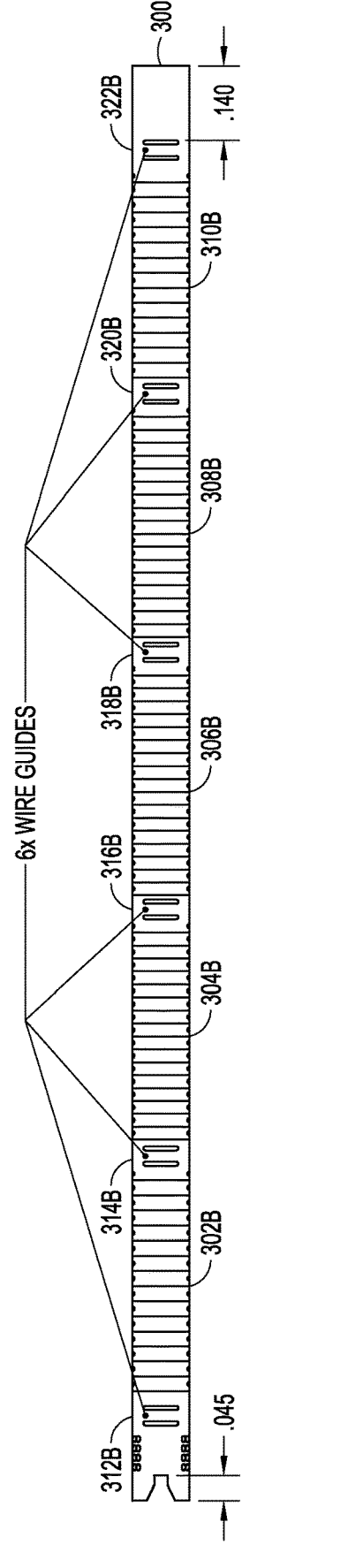
Figure 4A:
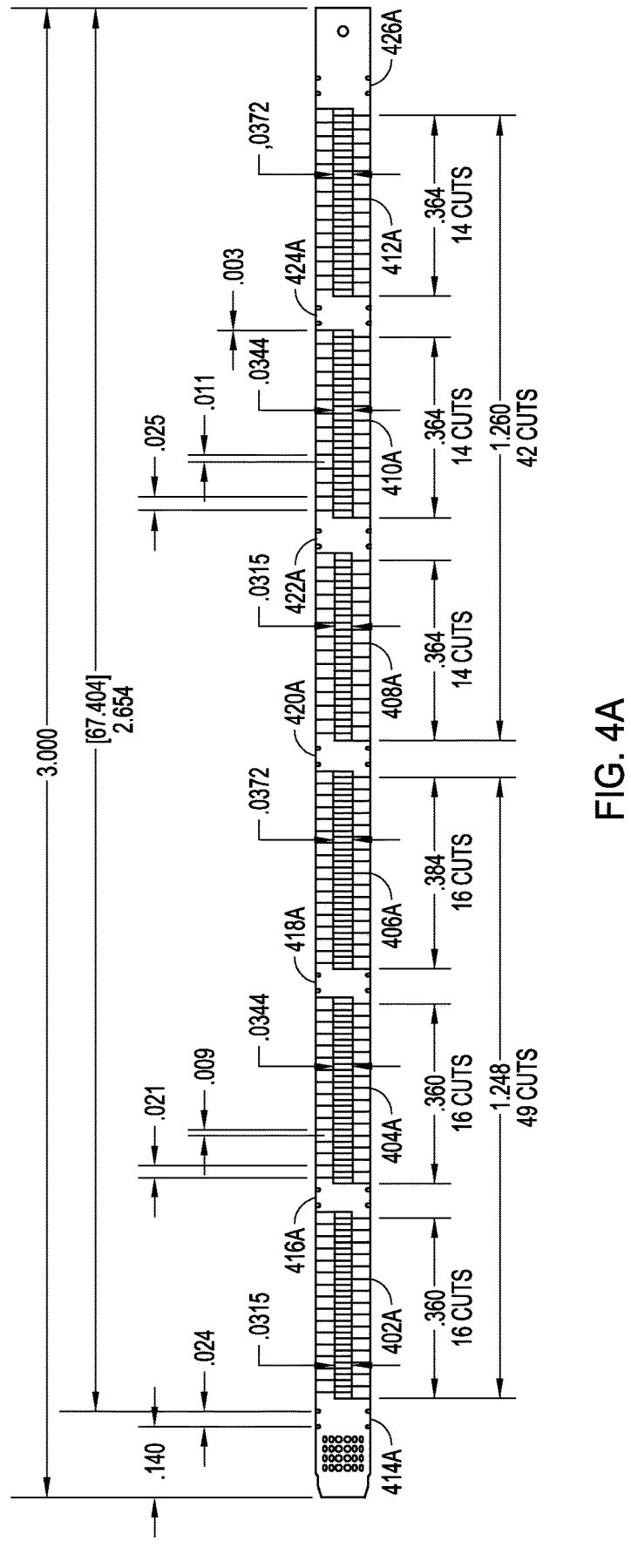
Figure 4B:
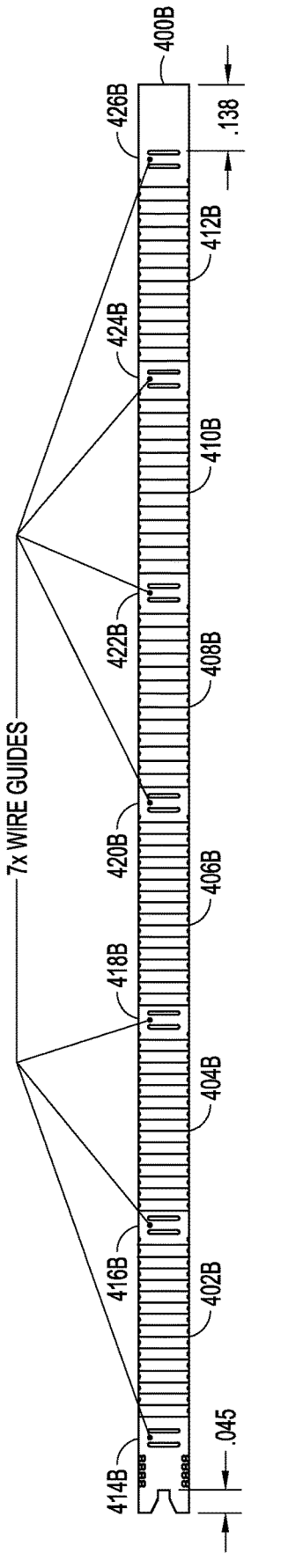
Figure 5A:
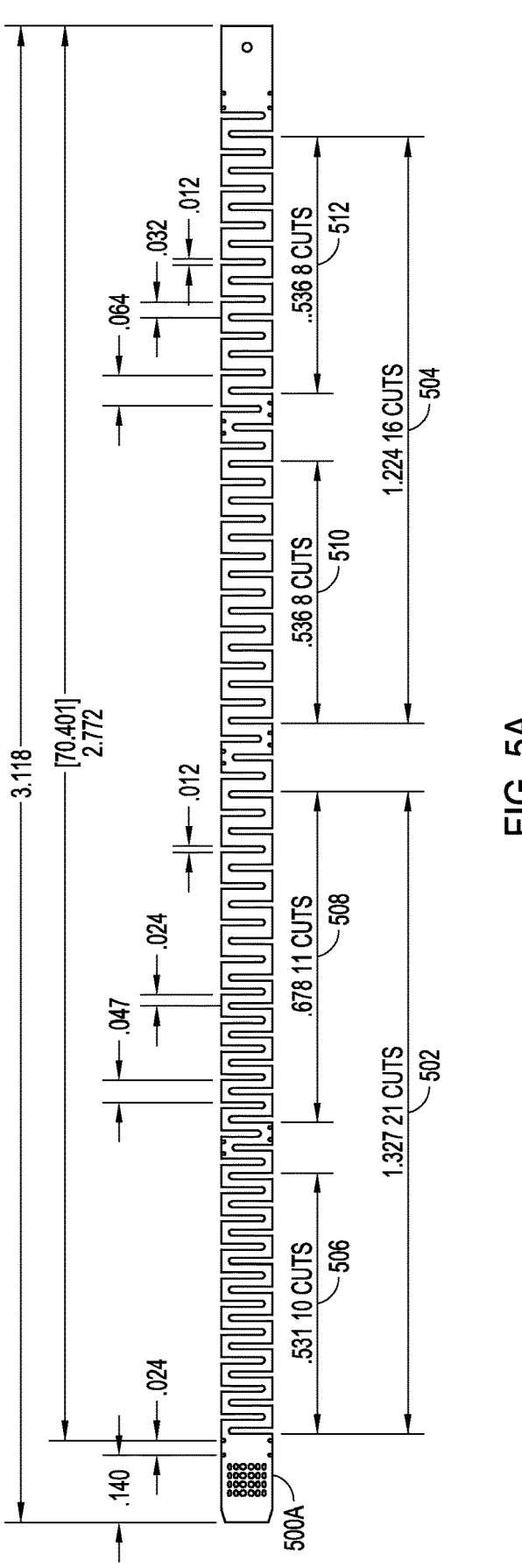
Figure 5B:
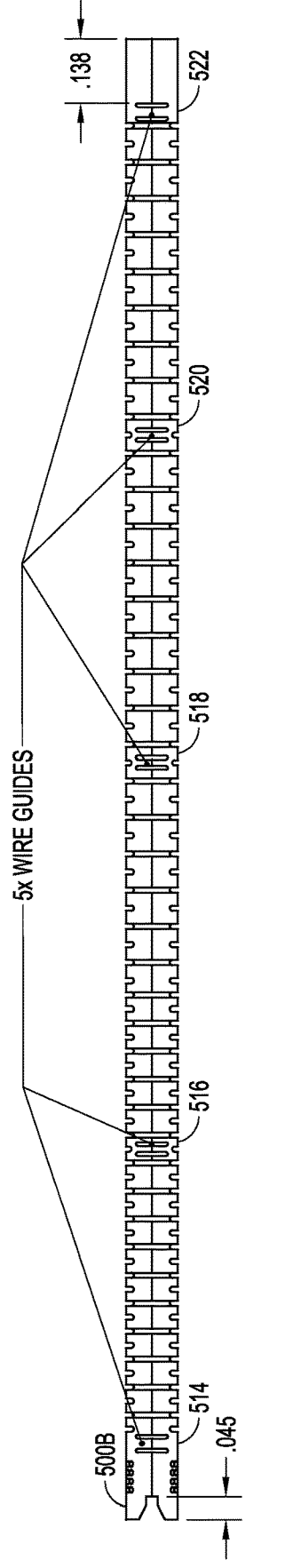

FIGS. 3A-5B illustrate examples of tubes with varying number of flexible sections containing different numbers of cuts, different cut widths, and a different number of wire guides to achieve different angles of articulation. FIGS. 3A, 4A, and 5A show a top down view of each respective tube, while FIGS. 3B, 4B, and 5B show a side view of each tube. FIGS. 3A-5B illustrate different representative embodiments of tubes with flexible sections of different lengths and number of cuts, different spacing between the flexible sections and different placement and number of wire guide locations. FIG. 3A illustrates an example of a tube 300A with a total length of 2.672 inches, and five flexible sections 302A, 304A, 306A, 308A, and 310A. The first flexible section 302 can include 15 total coarse and/or fine cuts (as described above) spanning 0.392 inches. In the first flexible section 302, the width of the fine cuts can vary from 0.003 inches to 0.025 inches. The distance between cuts (and thus the width of the "beams" between the cuts) can be 0.011 inches.

The second flexible section 304A can be 0.382 inches in length and can include 17 cuts. Further, the size (e.g., the width when looking at the tube 300A from above) of the switchback member can be 0.0344 inches. The second flexible section 304A can include 17 total cuts and span a length of 0.384 inches. The third flexible section 306A can include 18 total cuts and span a length of 0.408 inches. In the third flexible section 306A, a distance between the fine cuts (and thus the width of the central beams between the cuts) can range from 0.009 inches to 0.021 inches. The fourth flexible section 308A can include 18 cuts and span 0.408 inches of the tube 300A. A fifth flexible section 310A of the tube 300A can include 14 cuts and span a length of 0.364 inches. Similar to the dimensions of the cuts in the first flexible section 302, the cut width can vary from 0.003 inches to 0.025 inches and the beam width (or distance between cuts) can be 0.011 inches in the fifth flexible section 310.

As illustrated in FIGS. 3A and 3B, adjacent to the flexible sections, 302A-310A, and 302B-310B, there can be articulation member wire guide locations 312A-322A and 312B-322B. The wire guide locations 312-322 can be a "thicker" portion of the tube 300A, 300B (e.g., a portion of the tube 300A, 300B that has fewer cuts or no cuts), that separate the flexible sections 302-310 such as to allow an eyelet, loop, ring, or the like to be located inside the tube 300A, 300B such as to allow for an articulation member such as a pull wire to be situated on the inside of the tube 300A, 300B. The wire guide locations 312A-322A and 312B-322B can keep the articulation member in place along the inner diameter of the tube 300A, 300B so that when the articulation member is pulled, the flexible sections 312A-322A and 302B-310B can cause the distal end of the tube 300A, 300B to bend or deflect in the direction the articulation member is being pulled. As illustrated in FIG. 3B, wire guide location 322B, located toward the distal end of the tube 300B, can be located a distance from the tip of the tube 300B, such as 0.140 inches from the end of the tube 300B. The dimensions illustrated in FIGS. 3A and 3B can allow for an articulation angle of 263 degrees (e.g., at the distal end of the tube 300A, 300B. In such an example, bending or articulation can initiate in the middle three sections second flexible section 304A, third flexible section 306A, and five flexible sections 308A consisting of 53 total cuts and spanning 1.344 inches of the tube 300A.

As illustrated in FIGS. 4A and 4B, the length of the tube 400A, 400B (3.00 inches) can be longer than the example illustrated in FIGS. 3A and 3B. Further, the tube 400A, 400B can include six flexible sections 402A-412A and 402B-412B. The first flexible section 402A and the second flexible section 404A can each include 16 cuts and be a length of 0.360 inches. The third flexible section 406A can also include 16 cuts but can be a length of 0.384 inches. The fourth flexible section 408A, the fifth flexible section 410A, and the sixth flexible section 412A can all include 14 cuts and be a length of 0.364 inches. Such a configuration can essentially "split" or separate the tube 300A into two main portions, one that includes the first flexible section 402A, second flexible section 404A, and third flexible section 406A, including 49 cuts and spanning 1.248 inches, and a second one that includes the fourth flexible section 408A, the fifth flexible section 410A and the sixth flexible section 412A, including 42 cuts and spanning 1.260 inches. As shown in FIG. 4A, the cut widths can vary such as from 0.021 inches between the fine cuts in the second flexible section 404A and 0.025 between the fine cuts in the fifth flexible section 410A. Similarly, the beam width between the cuts can vary, such as 0.009 inches in the second flexible section 404A and 0.011 inches in the fifth flexible section 410A.

Also as illustrated in FIG. 4A, the size of the switchback members (as discussed above with respect to FIG. 3A) can vary along the length of the tube 400A (e.g., in the different flexible sections). For example, in the first flexible section 402A the size of the switchback members can be 0.0315 inches. In the second flexible section 404A the size of the switchback members can be 0.0344 inches, 0.072 inches in the third flexible section 406A, 0.0315 inches in the fourth flexible section 408A, 0.0344 inches in the fifth flexible section 410A, and 0.0372 inches in the sixth flexible section 412A. The width of the cuts in each section can be uniform or varied such as discussed above. The tube 400A, 400B can includes seven wire guide locations 414A-426A and 414B-426B, with the most distal wire guide location 426A, 426B located 0.138 inches away from the tip of the tube 400A, 400B. The dimensions illustrated in FIGS. 4A and 4B allow for an articulation angle of 292 degrees (e.g., at the distal end of the tube 400A, 400B).

FIGS. 5A and 5B illustrate a representative backbone of a tube 500A, 500B spanning 3.118 inches. The tube 500A, 500B, instead of having deflectable or flexible sections, as illustrated in FIGS. 3 and 4, has a backbone that is flexible along the entire length where the switchback members are formed. Different portions of the tube 500A, 500B can be made to have a different amount of flexibility by varying the size of the switchback members, the cut widths (and hence the central beam widths) in different portions of the tube 500A, 500B. As illustrated in 5A, the tube 500A may have cuts in a pattern such that there are adjacent switchback members spanning 2.772 inches of the length of the tube 500A. In an example, a first portion 506 of the tube 500A, can include 10 cuts and span 0.531 inches, and a second portion 508, of the tube 500A can include 11 cuts and span 0.678 inches. In the second portion 508, an edge of the switchback members can be 0.047 inches, the width of a central beam joining adjacent switchback members can be 0.024 inches, and a cut width of the cuts forming the switchback members can be 0.012 inches.

More distally, the tube 500A can include a third portion 510 including 8 cuts and spanning 0.536 inches and a fourth portion 512, including 8 cuts and spanning 0.536 inches. In the fourth portion 512, an edge of the switchback members can be 0.064 inches, the width of a central beam joining adjacent switchback members can be 0.032 inches, and a cut width of the cuts forming the switchback members can be 0.012 inches. The dimensions of the edge of the switchback members, the width of the central beams, and the cut widths can be uniform or varied as necessary to achieve a desired degree of deflection of the tube 500A, 500B.

FIG. 5B illustrates the tube of FIG. 5A rotated so as to show a side view. As illustrated in FIG. 5B, the tube 500B can include articulation member or wire guide locations 514, 516, 518, and 520.

As illustrated in the examples of FIGS. 3A-5B, the tubes can have any number of flexible portions or sections, any sized switchback members, any cut widths, or any number of wire guide locations as desired or necessary. For example, a tube may include five, six, or seven wire guide locations, may have cut widths of 0.003 inches, 0.0025 inches, 0.0032 inches, may have cut regions with different amounts of cuts and different beam widths in each of the proximal portion, distal portion, or the midsection of the tube. For example, a tube can have 14 cuts in the proximal portion with beam widths of 0.011 inches, one or more midsection portions with 17 or 18 cuts, and beam widths of 0.009 inches, and a distal portion with 15 cuts and a beam width of 0.011 inches.

In an example, a tube can have a proximal portion with 14 or 15 cuts, and a beam width of 0.011 inches and a distal portion with 17 or 18 cuts and a beam width of 0.009 inches. In an example, the tube can have a proximal portion with 14 cuts and a beam width of 0.011 inches and a distal portion with 16 or 17 cuts and a beam width of 0.009 inches. In an example, another tube can have a proximal portion with 12 cuts and a beam width of 0.011 inches, a midsection with 13 or 14 cuts and beam width of 0.009 inches, and a distal portion with 12 cuts and a beam width of 0.011 inches. In an example, the tube can have a proximal portion with 14 cuts and a beam width of 0.011 inches and a distal portion with 16 cuts and a beam width of 0.009 inches. A tube can be formed with multiple proximal, midsection, and distal portions as desired, and the cut widths, beam widths, switchback member shape and/or dimensions, and wire guide locations can be any of or any combination of those described in the various examples discussed above.

Figure 6:
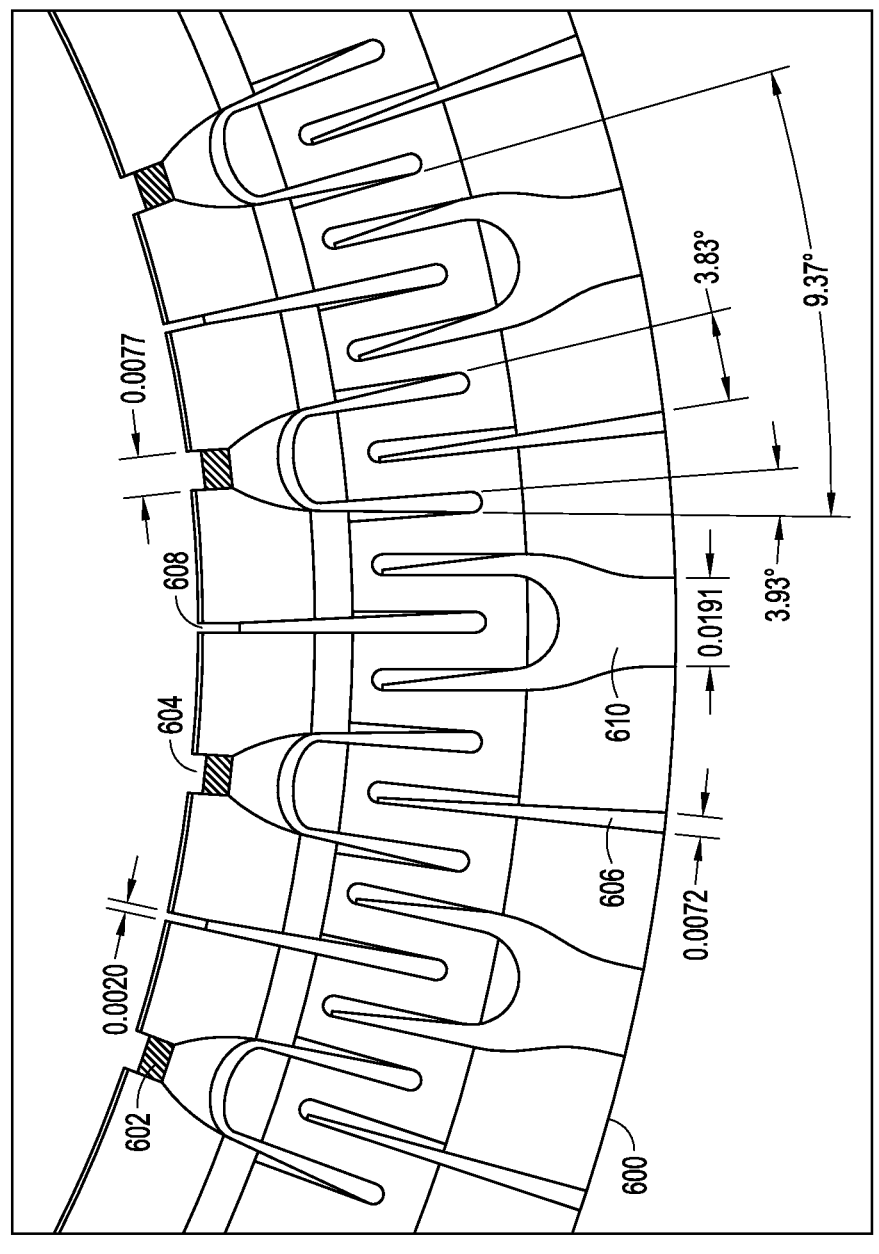
FIG. 6 illustrates an example of a tube with opposing open or closed cuts during active articulation.

FIG. 6 illustrates an example of a tube with open and opposing closed cuts during active articulation. FIG. 6 illustrates an example of a tube 600 with an alternating coarse cut and fine cut pattern such as those discussed above. As illustrated in FIG. 6, articulation member 602 such as a wire or cable can be located along an inner portion of the tube 600, such that when the articulation member 602 is pulled or otherwise engaged, coarse cut 604 is pulled or articulated to a narrower width when compared to a neutral cut thickness, to a width of 0.0077 inches, and fine cut 608 adjacent to coarse cut 604 is pulled to a width of 0.0020 inches, which can be a narrower width than its neutral thickness. On the opposing side of the tube 600 cylinder, fine cut 606, which opposes coarse cut 604 can be bent or articulated to a wider thickness (e.g., 0.0072 inches) compared to its neutral starting thickness in the absence of bending. Similarly, coarse cut 610, which is adjacent to fine cut 606 can be articulated to a wider thickness (e.g., 0.0191 inches) compared to its neutral or starting thickness in the absence of bending.

Pulling or maneuvering the articulation member 602 can cause different portions of the tube 600 to bend at different angles, such as those illustrated in FIG. 6. For example, smaller portions of the tube 600 can bend at smaller angles (e.g., 3.93 degrees, 3.83 degrees, etc.) and cause larger portions of the tube 600 to bend at larger angles, such as 9.37 degrees.

Generally, the wider the neutral cut width of the coarse cuts are, the more material is being moved when the tube is deflected or bent. This results in a "tighter" bend and allows for the fine cuts to expand (widen) to provide some "give" and allow the coarse cuts to contract toward each other during the bending action. The tubes described herein can be designed to reach targeted portions of anatomy such as the calyx of the kidney, including the lower calyx, which can involve a tight aggressive turn of the tube in order for the scope to reach it. Therefore, as discussed above, different tubes can be designed with different dimensions, such as different sized cut widths, different number of cuts, or the like, such that an articulation or flexible section can bend at angles greater than 180 degrees (e.g., 250 degrees, 270 degrees, 300 degrees, or larger).

Figure 7B:
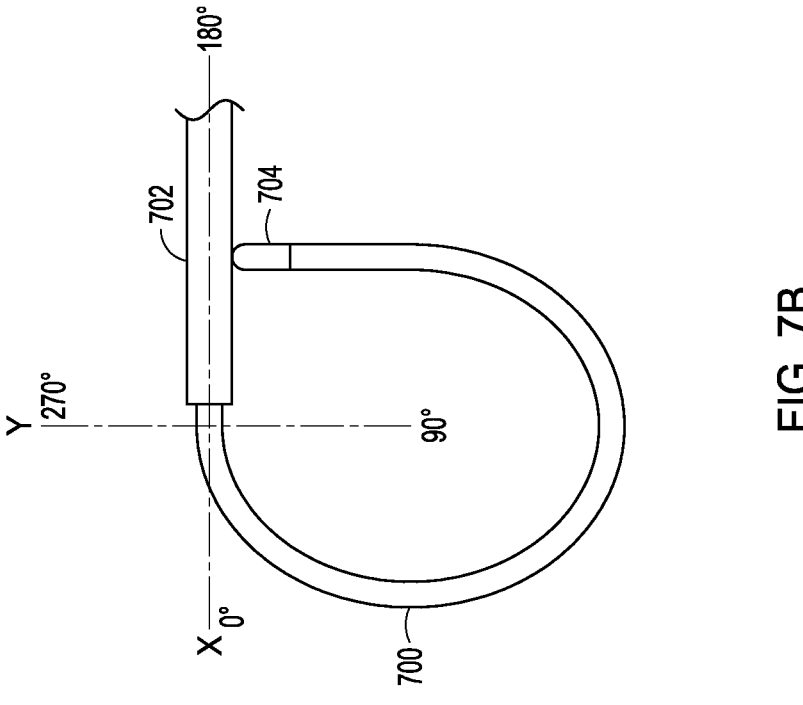
FIGS. 7A and 7B illustrate an example of a fine and coarse cut backbone articulation.
Figure 7A:
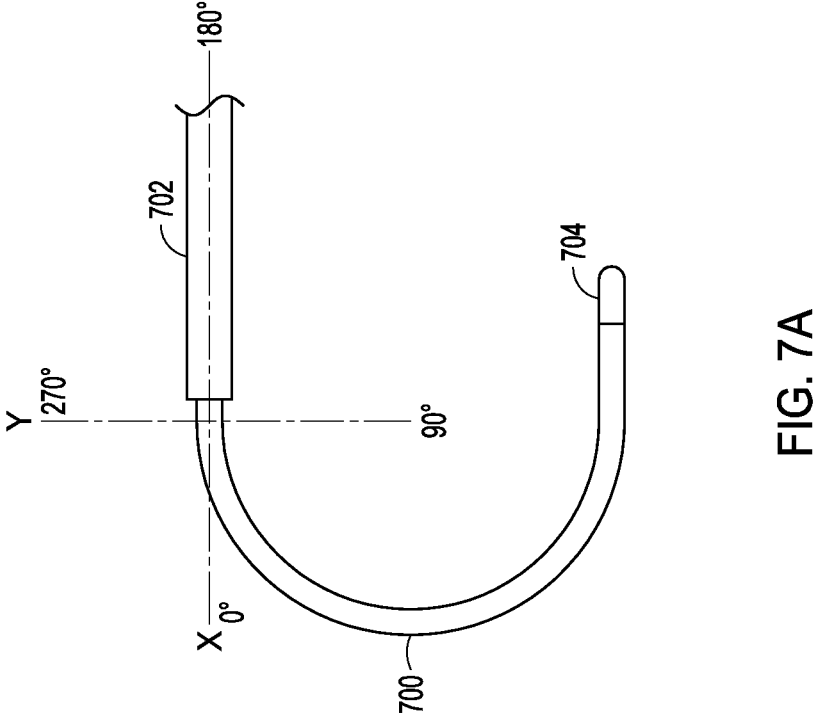

FIGS. 7A and 7B illustrate an example of a fine/coarse cut backbone articulation. As illustrated in FIGS. 7A and 7B, an articulating backbone 700 (e.g., a deflectable backbone, articulating tube, etc.) with an alternating coarse cut/fine cut pattern such as those described above, can be attached to a non-articulation solid or more rigid member 702 such as a scope, handle, or the like. The articulating backbone 700 can be bent in such a way that the tip 704 of the articulating backbone 700 can be bent from a straight position (a 0 degree angle) to an angle greater than 270 degrees as illustrated in FIG. 7A to an angle of over 300 degrees as illustrated in FIG. 7B.

Figure 8:
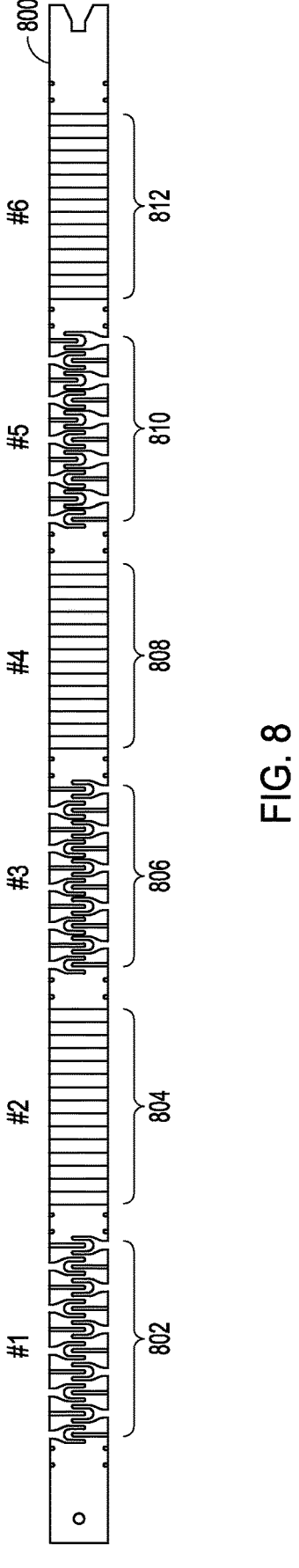
FIG. 8 illustrates an example of a tube with flexible sections constructed with features arranged at a rotational angle with respect to each other.

FIG. 8 illustrates an example of a tube with flexible sections constructed with features arranged at a rotational angle with respect to each other. FIG. 8 illustrates an example of a patterned tube 800 similar to that illustrated in FIG. 1, with multiple flexible sections 802-812. FIG. 8 again shows a "top down" view of the patterned tube 800. In the example illustrated in FIG. 8, at least a portion of the second flexible section 804 can be constructed with features arranged at a rotational angle with respect to the first flexible section 802. For example, one or more of the switchback members in the second flexible section 804 can be arranged at a rotational angle (e.g., 90 degrees, 180 degrees, or the like) to the switchback members in the first flexible section 802. In such an example, the switchback members in the second flexible section 804 can be located such that they are on a side of the patterned tube 800 cylinder when looking top down at the switchback members in the first flexible section 802.

Such a pattern can repeat through the length of the patterned tube 800. For example, the third flexible section 806 and the fifth flexible section 810 can have the same orientation as the first flexible section 802, while the fourth flexible section 808 and the sixth flexible section 812 can have the same orientation as second flexible section 804. In such an example each adjacent section will have features rotated with respect to each other or offset from each other.

This may allow the patterned tube 800 to operate like a laser cut helical spring and allow for the patterned tube 800 to be deflected in two separate planes (e.g., planes oriented orthogonal to one another). Those sections in the same 90-degree line (e.g., first flexible section 802, third flexible section 806, and fifth flexible section 810) can bend or be deflected in a first plane, and the other sections (second flexible section 804, fourth flexible section 808, and sixth flexible section 812) can bend in a second plane. Additionally, or alternatively, adjacent switchback members in the same flexible section can be rotated with respect to one another so that a portion of each flexible section can be deflected in separate planes.

Figure 9:
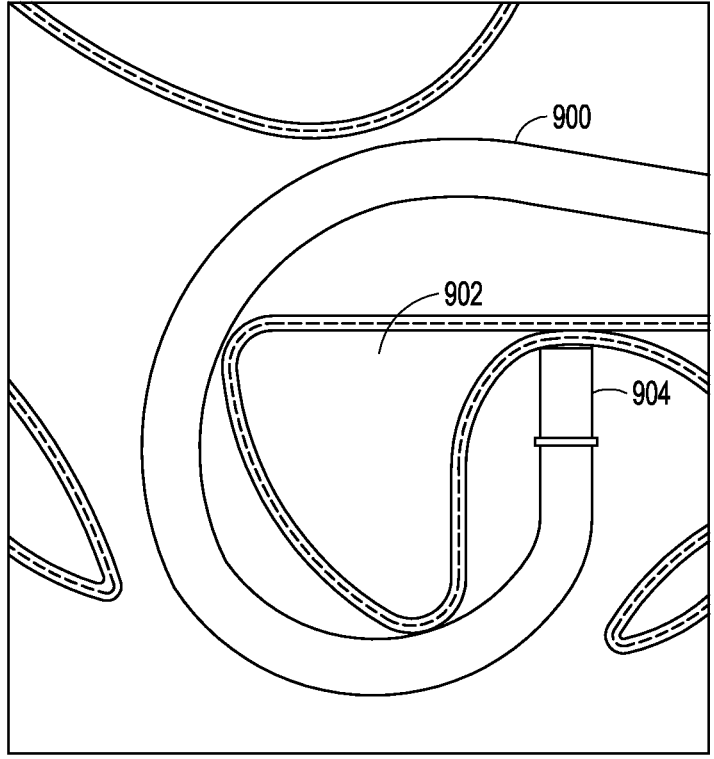
FIG. 9 illustrates an example of a fine and coarse cut backbone incorporated into an endoscope shaft articulation performance in simulated use.

FIG. 9 illustrates an example of a fine/coarse cut backbone incorporated into an endoscope shaft articulation performance in simulated use. As illustrated in FIG. 9, and endoscope 900 with a backbone employing a pattern of alternating cuts such as described herein, is illustrated in use in a modeled portion of anatomy 902. The modeled portion of anatomy 902 can represent a portion of human anatomy such as the calyx of a kidney in which the endoscope 900 can be inserted during a medical procedure, such as kidney stone ablation. In the example of FIG. 9, the modeled portion of anatomy 902 includes a cavity 904, in which a stone, tumor, or the like, can form. The tip of the endoscope 900 can maneuver or bend around a piece of tissue represented by the oblong shaped section of the modeled portion of anatomy 902 so that a procedure such a stone ablation can be performed in the cavity 904 by emitting laser radiation from the tip of the endoscope 900.

ADDITIONAL NOTES AND EXAMPLES

Example 1 is a patterned tube permitting articulation of a medical scope, the patterned tube comprising: at least one flexible section between a proximal end of the patterned tube and a distal end of the patterned tube, the at least one flexible section including: multiple first cuts having a first cut thickness; multiple second cuts having a second cut thickness, wherein particular ones of the second cuts are located substantially opposite laterally across the patterned tube from particular ones of the first cuts and separated therefrom by switchback members; and one or more bending moment transfer members, wherein particular ones of the one or more bending moment transfer members are located between adjacent particular ones of the first cuts and also between adjacent particular ones of the second cuts and connect adjacent switchback members.

In Example 2, the subject matter of Example 1 optionally includes wherein the one or more bending moment transfer members respectively include a circumferential portion extending about an outer circumference of the patterned tube and configured to transfer a bending moment to a switchback member formed in the patterned tube between a particular one of the first cuts and a particular one of the second cuts.

In Example 3, the subject matter of Example 2 optionally includes wherein the switchback member is configured to cause a particular first cut to do one of widen or narrow and to cause an opposing particular second cut to do the other of widen or narrow during an articulation of a portion of the patterned tube including the particular first cut and the opposing particular second cut.

In Example 4, the subject matter of Example 3 optionally includes an articulation member attached to an inside portion of the patterned tube.

In Example 5, the subject matter of Example 4 optionally includes wherein the articulation member is attached to the inside portion of the patterned tube by at least one guide configured to maintain a position of the articulation member along the flexible section and to enable deflection of at least a portion of the flexible section when the articulation member is retracted via a manipulator.

In Example 6, the subject matter of any one or more of Examples 4-5 optionally include wherein the articulation member includes a cable or a wire.

In Example 7, the subject matter of any one or more of Examples 1-6 optionally include wherein a neutral thickness of the multiple first cuts and a neutral thickness of the multiple second cuts are varied along at least a portion of the at least one flexible section.

In Example 8, the subject matter of Example 7 optionally includes wherein in a neutral state a particular first cut at a distal end of the flexible section is wider than a particular first cut at a proximal end of the flexible section.

In Example 9, the subject matter of any one or more of Examples 7-8 optionally include wherein in a neutral state a particular second cut at a distal end of the flexible section is wider than a particular second cut at a proximal end of the flexible section.

In Example 10, the subject matter of any one or more of Examples 1-9 optionally include a first flexible section; and a second flexible section located adjacent to the first flexible section.

In Example 11, the subject matter of Example 10 optionally includes wherein at least a portion of the second flexible section is constructed with at least one cut arranged at a rotational angle with respect to at least one cut in the first flexible section.

In Example 12, the subject matter of any one or more of Examples 10-11 optionally include wherein the first flexible section is formed from a different material than the second flexible section.

In Example 13, the subject matter of Example 12 optionally includes wherein the material of the first flexible section and the material of the second flexible section have a different flexibility.

In Example 14, the subject matter of any one or more of Examples 1-13 optionally include wherein an outer diameter of the patterned tube at the distal end of the patterned tube is smaller than an outer diameter at the proximal end of the patterned tube.

In Example 15, the subject matter of any one or more of Examples 1-14 optionally include wherein at least one of a portion of a particular first cut or a at least one portion of a particular second cut is tapered to accommodate a particular switchback member located within at least a portion thereof.

Example 16 is a patterned tube for permitting articulation of a medical scope, the tube comprising: a first flexible section; and a second flexible section located adjacent to the first flexible section; wherein the first flexible section and the second flexible section include: multiple first cuts having a first cut thickness; multiple second cuts having a second cut thickness, wherein particular ones of the second cuts are located substantially opposite laterally across the tube from particular ones of the first cuts and separated therefrom by switchback members; and one or more bending moment transfer members, wherein particular ones of the one or more bending moment transfer members are located between adjacent particular ones of the first cuts and also between adjacent particular ones of the second cuts and connect adjacent switchback members.

In Example 17, the subject matter of Example 16 optionally includes wherein a neutral thickness of the multiple first cuts and a neutral thickness of the multiple second cuts are varied along at least a portion of at least one of the first flexible section or the second flexible section.

In Example 18, the subject matter of Example 17 optionally includes wherein in a neutral state at least one of: a particular first cut at a distal end of the first flexible section is wider than a particular first cut at a proximal end of the first flexible section; or a particular second cut at the distal end of the first flexible section is wider than a particular second cut at the proximal end of the first flexible section.

In Example 19, the subject matter of any one or more of Examples 17-18 optionally include wherein in a neutral state at least one of: a particular first cut at a distal end of the second flexible section is wider than a particular first cut at a proximal end of the second flexible section; or a particular second cut at the distal end of the second flexible section is wider than a particular second cut at the proximal end of the second flexible section.

Example 20 is a patterned deflectable portion of a medical device shaft, the deflectable portion comprising: a first flexible section; a second flexible section located adjacent to the first flexible section; and an articulation member attached to an inside portion of the deflectable portion by at least one guide configured to maintain a position of the articulation member along the flexible section and to enable deflection of at least a portion of the flexible section when the articulation member is retracted via a manipulator;

wherein the first flexible section and the second flexible section include: multiple first cuts having a first cut thickness; multiple second cuts having a second cut thickness, wherein particular ones of the second cuts are located substantially opposite laterally across the deflectable portion from particular ones of the first cuts and separated therefrom by switchback members; and one or more bending moment transfer members, wherein particular ones of the one or more bending moment transfer members are located between adjacent particular ones of the first cuts and also between adjacent particular ones of the second cuts and connect adjacent switchback members.

In Example 21, the subject matter of Example 20 optionally includes wherein in a neutral state at least one of: a particular first cut at a distal end of the first flexible section is wider than a particular first cut at a proximal end of the first flexible section; a particular second cut at the distal end of the first flexible section is wider than a particular second cut at the proximal end of the first flexible section; a particular first cut at a distal end of the second flexible section is wider than a particular first cut at a proximal end of the second flexible section; or a particular second cut at the distal end of the second flexible section is wider than a particular second cut at the proximal end of the second flexible section.

In Example 22, the subject matter of any one or more of Examples 20-21 optionally include wherein at least a portion of the second flexible section is constructed with at least one cut arranged at a rotational angle with respect to at least one cut in the first flexible section, and wherein the first flexible section is formed from a different material than the second flexible section.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A patterned tube permitting articulation of a medical scope, the patterned tube comprising:
   at least one flexible section in between a proximal end of the patterned tube and a distal end of the patterned tube, the at least one flexible section including:
   multiple first cuts having a first cut thickness, wherein each cut of the multiple first cuts has a bifurcated end bifurcating into two end cut portions;
   multiple second cuts having a second cut thickness, wherein particular ones of the multiple second cuts are located substantially opposite laterally across the patterned tube from particular ones of the multiple first cuts and separated therefrom by switchback members, and wherein each cut of the multiple second cuts has an end portion positioned between the two end cut portions of the bifurcated end of an opposing first cut; and
   one or more bending moment transfer members, wherein:
      particular ones of the one or more bending moment transfer members are located between adjacent first cuts and also between adjacent second cuts and connect adjacent switchback members; and
      a stiffness of the one or more bending moment transfer members is varied between at least two longitudinally spaced apart bending moment transfer members along a length of the patterned tube.

2. The patterned tube of claim 1, wherein the one or more bending moment transfer members respectively include a circumferential portion extending about an outer circumference of the patterned tube and configured to transfer a bending moment to a switchback member formed in the patterned tube between a first particular one of the multiple first cuts and a first particular one of the multiple second cuts, wherein the first particular one of the multiple first cuts opposes the first particular one of the multiple second cuts.

3. The patterned tube of claim 2, wherein the switchback member is configured to cause the first particular one of the multiple first cuts to do one of widen or narrow and to cause the first particular one of the multiple second cuts to do the other of widen or narrow during an articulation of a portion of the patterned tube including the first particular one of the multiple first cuts and the opposing first particular one of the multiple second cuts.

4. The patterned tube of claim 3, further comprising:
   an articulation member attached to an inside portion of the patterned tube.

5. The patterned tube of claim 4, wherein the articulation member is attached to the inside portion of the patterned tube by at least one guide configured to maintain a position of the articulation member along the at least one flexible section and to enable deflection of at least a portion of the at least one flexible section when the articulation member is retracted via a manipulator.

6. The patterned tube of claim 4, wherein the articulation member includes a cable or a wire.

7. The patterned tube of claim 2, wherein a neutral thickness of the multiple first cuts and a neutral thickness of the multiple second cuts are varied along at least a portion of the at least one flexible section.

8. The patterned tube of claim 7, wherein in a neutral state the first particular one of the multiple first cuts at a distal end of the at least one flexible section is wider than a second particular one of the multiple first cuts at a proximal end of the at least one flexible section.

9. The patterned tube of claim 7, wherein in a neutral state the first particular one of the multiple second cuts at a distal end of the at least one flexible section is wider than a second particular one of the multiple second cuts at a proximal end of the at least one flexible section.

10. The patterned tube of claim 1, further comprising:
   a first flexible section; and
   a second flexible section located adjacent to the first flexible section.

11. The patterned tube of claim 10, wherein at least a portion of the second flexible section is constructed with at least one cut arranged at a rotational angle with respect to at least one cut in the first flexible section.

12. The patterned tube of claim 10, wherein the first flexible section is formed from a different material than the second flexible section.

13. The patterned tube of claim 12, wherein the material of the first flexible section and the material of the second flexible section have a different flexibility.

14. The patterned tube of claim 1, wherein an outer diameter of the patterned tube at the distal end of the patterned tube is smaller than an outer diameter at the proximal end of the patterned tube.

15. The patterned tube of claim 1, wherein at least one of a portion of a particular first cut or at least one portion of a particular second cut is tapered to accommodate a particular switchback member located within at least a portion thereof.

16. A patterned tube for permitting articulation of a medical scope, the patterned tube comprising:
   a first flexible section; and
   a second flexible section located adjacent to the first flexible section, wherein the first flexible section and the second flexible section include:
      multiple first cuts having a first cut thickness, wherein each cut of the multiple first cuts has a bifurcated end bifurcating into two end cut portions;
      multiple second cuts having a second cut thickness, wherein particular ones of the multiple second cuts are located substantially opposite laterally across the patterned tube from particular ones of the multiple first cuts and separated therefrom by switchback members, and wherein each cut of the multiple second cuts has an end portion positioned between the two end cut portions of the bifurcated end of an opposing first cut; and
      one or more bending moment transfer members, wherein:
         particular ones of the one or more bending moment transfer members are located between adjacent first cuts and also between adjacent second cuts and connect adjacent switchback members;
         the one or more bending moment transfer members include a central beam and a circumferential portion extending about an outer circumference of the patterned tube and configured to cooperate in conjunction with each other to transfer a bending moment to a particular switchback member; and a stiffness of the one or more bending moment transfer members is varied between at least two longitudinally spaced apart bending moment transfer members along a length of the patterned tube.

17. The patterned tube of claim 16, wherein a neutral thickness of the multiple first cuts and a neutral thickness of the multiple second cuts are varied along at least a portion of at least one of the first flexible section or the second flexible section.

18. The patterned tube of claim 17, wherein in a neutral state at least one of:

a first particular one of the multiple first cuts at a distal end of the first flexible section is wider than a second particular one of the multiple first cuts at a proximal end of the first flexible section; or a first particular one of the multiple second cuts cut at the distal end of the first flexible section is wider than a second particular one of the multiple second cuts at the proximal end of the first flexible section.

19. The patterned tube of claim 17, wherein in a neutral state at least one of:

a first particular one of the multiple first cuts at a distal end of the second flexible section is wider than a second particular one of the multiple first cuts at a proximal end of the second flexible section; or a first particular one of the multiple second cuts at the distal end of the second flexible section is wider than a second particular one of the multiple second cuts at the proximal end of the second flexible section.

20. A patterned deflectable portion of a medical device shaft, the patterned deflectable portion comprising:

a first flexible section;

a second flexible section located adjacent to the first flexible section; and an articulation member attached to an inside portion of the patterned deflectable portion by at least one guide configured to maintain a position of the articulation member along at least one of the first flexible section or the second flexible section and to enable deflection of at least a portion of at least one of the first flexible section or the second flexible section when the articulation member is retracted via a manipulator, wherein the first flexible section and the second flexible section include:

multiple first cuts having a first cut thickness, wherein each cut of the multiple first cuts has a bifurcated end bifurcating into two end cut portions;

multiple second cuts having a second cut thickness, wherein particular ones of the multiple second cuts are located substantially opposite laterally across the patterned deflectable portion from particular ones of the multiple first cuts and separated therefrom by switchback members, and wherein each cut of the multiple second cuts has an end portion positioned between the two end cut portions of the bifurcated end of an opposing first cut; and one or more bending moment transfer members, wherein;

particular ones of the one or more bending moment transfer members are located between adjacent first cuts and also between adjacent second cuts and connect adjacent switchback members;

the one or more bending moment transfer members include a central beam and a circumferential portion extending about an outer circumference of the patterned deflectable portion and configured to cooperate in conjunction with each other to transfer a bending moment to a particular switchback member; and a stiffness of the one or more bending moment transfer members is varied between at least two longitudinally spaced apart bending moment transfer members along a length of the patterned deflectable portion.

21. The patterned deflectable portion of claim 20, wherein in a neutral state at least one of:

a first particular one of the multiple first cuts at a distal end of the first flexible section is wider than a second particular one of the multiple first cuts at a proximal end of the first flexible section;

a first particular one of the multiple second cuts at the distal end of the first flexible section is wider than a second particular one of the multiple second cuts at the proximal end of the first flexible section;

a third particular one of the multiple first cuts at a distal end of the second flexible section is wider than a fourth particular one of the multiple first cuts at a proximal end of the second flexible section; or a third particular one of the multiple second cuts at the distal end of the second flexible section is wider than a fourth particular one of the multiple second cuts at the proximal end of the second flexible section.

22. The patterned deflectable portion of claim 20, wherein at least a portion of the second flexible section is constructed with at least one cut arranged at a rotational angle with respect to at least one cut in the first flexible section, and wherein the first flexible section is formed from a different material than the second flexible section.

23. The patterned tube of claim 1, wherein the variation in stiffness between the at least two longitudinally spaced apart bending moment transfer members along the length of the patterned tube allows for selection and adjustment of an articulation pathway and sweep path of the distal end.

* * * * *